US007803763B2

(12) United States Patent
Thurow et al.

(10) Patent No.: US 7,803,763 B2
(45) Date of Patent: Sep. 28, 2010

(54) METHOD OF PURIFYING PREPROINSULIN

(75) Inventors: Horst Thurow, Hambach (DE); Hans Blumenstock, Hattersheim (DE); Chantalle Havenith, Hofheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/305,508

(22) Filed: Dec. 15, 2005

(65) Prior Publication Data

US 2006/0183666 A1    Aug. 17, 2006

Related U.S. Application Data

(63) Continuation of application No. 10/632,414, filed on Aug. 1, 2003, now abandoned.

(60) Provisional application No. 60/433,726, filed on Dec. 16, 2002.

(30) Foreign Application Priority Data

Aug. 1, 2002    (DE) ............................... 102 35 168

(51) Int. Cl.
*A61K 38/28*    (2006.01)
(52) U.S. Cl. .......................................... 514/3; 530/303
(58) Field of Classification Search ........................ None
See application file for complete search history.

(56) References Cited

U.S. PATENT DOCUMENTS

| 4,783,441 | A |   | 11/1988 | Thurow et al. |
|-----------|---|---|---------|---------------|
| 5,101,013 | A |   | 3/1992  | Dorschug et al. |
| 5,473,049 | A |   | 12/1995 | Obermeier et al. |
| 5,952,461 | A |   | 9/1999  | Kim et al. |
| 5,986,048 | A | * | 11/1999 | Rubroder et al. ............ 530/303 |

FOREIGN PATENT DOCUMENTS

| EP | 0 600 372  | A1 | * | 11/1993 |
| EP | 0264250    |    |   | 12/1994 |
| EP | 0489 780   | B1 | * | 11/1996 |
| WO | WO 91/03550|    |   | 3/1991  |
| WO | WO 99/33988|    |   | 7/1999  |
| WO | WO 01/25278|    |   | 4/2001  |

OTHER PUBLICATIONS

Seino et al. Sequences of Primate Insulin Genes Support the Hypothesis of a Slower Rate of Molecular Evolution in Humans and Apes than in Monkeys. Mol. Biol. Evol. 1992. vol. 9 No. 2, pp. 193-203.*
Majors. Column Pressure Considerations in Analytical Chemistry. Chromatography Online. 2007. pp. 1-11.*
Brange, J., et. al., Toward Understanding Insulin Fibrillation, Journal of Pharmaceutical Sciences, vol. 86, No. 5 May 1997.
Cowley, D.J., et. al., Expression, Purification and Characterization of Recombinant Human Proinsulin, FEBS Letters, (1997), vol. 402, pp. 124-130.
De Bernardez, E., et.. al., Inhibition of Aggregation Side Reactions during in Vitro Protein Folding , Methods in Enzymology, vol. 39, pp. 217-236 (1999).
Kemmler, W., et. al., Studies on the Conversion of Proinsulin to Insulin, The Journal of Biological Chemistry vol. 246, No. 22 pp. 6786-6791, (1971).
Ladisch, M.R., et. al., Recombinant Human Insulin, Biotechnol. Prog., (1992), vol. 8, pp. 469-478.
Ratner, R., et. al., Persistent Cutaneous Insulin Allergy Resulting from High-Molecular-Weight Insulin Aggregates , Diabetes, vol. 39, (1990) pp. 728-733.
Steiner, D.F., et. al., Isolation and Properties of PRoinsulin, Intermediate Forms, and Other Minor Components from Crystalline Bovine Insulin, Diabetes, vol. 17, No. 12 pp. 725-736 (1968).
Thurow, H., et. al., Stabilisation of Dissolved proteins against Denaturation at Hydrophobic Interfaces, Diabetologia (1984), vol. 27, pp. 212-218.
Ion Exchange Chromatography (IEC), Access online at http://www.proteinchemist.com/tutorial/iec.html (2005) 3pgs.
Methacrylate Adsorbent Resins, Sorbent Technologies Accessed online at http://sorbtech.com/catalog/catPage1380.htm (2005) 2pgs.
Protoporphyrin Gold Salt, Abstract-Pub-No. JP 63021093B. 2pgs, (1988).

* cited by examiner

*Primary Examiner*—Marcela M Cordero Garcia
(74) *Attorney, Agent, or Firm*—Balaram Gupta

(57) ABSTRACT

The invention relates to a method for the chromatographic purification of preproinsulins, in which higher molecular weight substances are removed from an aqueous solution of preproinsulin by a first chromatography on an anion exchanger in flow-through mode and a subsequent second chromatography on a cation exchanger in adsorption mode, and to a method for preparing insulins, which includes the method for preparing preproinsulins.

4 Claims, No Drawings

METHOD OF PURIFYING PREPROINSULIN

Approximately 12 million people worldwide suffer from type 1 diabetes mellitus which is characterized by an insufficient indigenous production of the hormone insulin. Substitution of the lack of endocrine insulin secretion by applying insulin preparations is the only possible form of therapy for this type of diabetes mellitus.

Insulin preparations are pharmaceutical preparations whose active substance is the hormone insulin. Here, insulin analogs and insulin derivatives are used in addition to naturally occurring insulins.

Human insulin which is produced in the human pancreas is a polypeptide comprising 51 amino acid residues which divide into two peptide chains: the A chain having 21 amino acid residues and the B chain having 30 amino acid residues. The sequence of the amino acid residues in both peptide chains has been genetically determined and is known. Both chains are connected to one another by two disulfide bridges. In addition, the A chain also contains an intrachain disulfide bridge.

Insulin analogs differ from human insulin by substitution of at least one amino acid residue and/or addition or removal of at least one amino acid residue. Insulin analogs may either occur naturally in species other than humans or may have been prepared artificially. Insulin derivatives contain chemically modified amino acid residues which contain, for example, additional ester or amido groups but otherwise show the human or an analog amino acid sequence.

Normally, insulin analogs or insulin derivatives exhibit an altered action kinetics compared to unmodified human insulin.

For some years, human insulin and the insulin analogs or insulin derivatives have been prepared by recombinant DNA technology. In industrial methods, for example, first an appropriate precursor of the formula 1, the preproinsulin (PPI), is prepared from which human insulin or the insulin analogs are prepared by enzymic cleavage.

For example, a genetic method for preparing human insulin comprises the following method steps:
a) Fermentation of the genetically modified microorganisms,
b) Harvesting said microorganisms and cell disruption,
c) Isolating the inclusion bodies containing the undissolved fusion protein,
d) Dissolving said fusion protein with correct folding of the peptide chain and with simultaneous closure of the disulfide bridges to give preproinsulin,
e) Enzymic cleavage of preproinsulin to give human insulin,
f) Purification of human insulin,
g) Crystallization of human insulin and drying of the obtained product.

When preparing an insulin analog, the amino acid sequence (of the A and B chains) in the appropriate regions of preproinsulin has already been predetermined. Enzymic cleavage of the various preproinsulins is carried out using proteases such as, for example, the enzyme trypsin and in addition, if necessary, the enzyme carboxypeptidase B.

The preproinsulin is a protein of the formula 1,

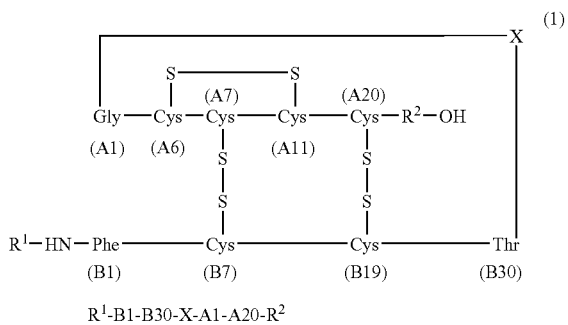

$R^1$-B1-B30-X-A1-A20-$R^2$ in which
X a) is a genetically encodable amino acid residue or
   b) is a peptide having from 2 to 35 amino acid residues, which starts and ends with in each case a basic amino acid residue, in particular Arg, and which, if it consists of more than 3 amino acid residues, starts and ends with in each case two basic amino acid residues, in particular Arg and/or Lys,
$R^1$ a) is hydrogen,
   b) is a genetically encodable amino acid residue or
   c) is a peptide having from 2 to 15 amino acid residues,
$R^2$ is a genetically encodable amino acid residue, and and the residues A1-A20 correspond to the amino acid sequence of the A chain of human insulin or of an insulin analog and the residues B1-B30 correspond to the amino acid sequence of the B chain of human insulin or of an insulin analog.

The preproinsulin is preferably a protein of the formula 1 in which

X is a peptide having 35 amino acid residues with the C-chain sequence of human insulin or simian insulin or is a peptide having 29 amino acids of the sequence:

```
                                        (SEQ ID NO: 1)
Arg-Asp-Val-Pro-Gln-Val-Glu-Leu-Gly-Gly-Gly-Pro-

Gly-Ala-Gly-Ser-Leu-Gln-Pro-Leu-Ala-Leu-Glu-Gly-

Ser-Leu-Gln-Lys-Arg
```

$R^1$ is a peptide having from 2 to 15 amino acid residues, whose carboxyl-terminal amino acid residue is Arg,
$R^2$ is the amino acid residue Asn or Gly,
and the residues A1-A20 correspond to the amino acid sequence of the A chain of human insulin and the residues B1-B30 correspond to the amino acid sequence of the B chain of human insulin or of an insulin analog in which Lys replaces Asn in position B3 and Glu replaces Lys in position B29.

The process stage—dissolving the fusion protein with correct folding of the peptide chain and with simultaneous closure of the disulfide bridges to give preproinsulin—produces, in addition to the desired monomeric preproinsulin, also polymeric forms of preproinsulin in a competing reaction. Said polymeric preproinsulins can be detected, owing to their higher molecular weight, by HPLC-GPC analysis or by the method of dynamic light scattering. In order to repress this undesired competing reaction, the initial concentration of the fusion protein needs to be as low as possible (De Bernadez et al., Meth. Enzym. 309:217, 1999). In practice, this process stage produces preproinsulin at a concentration of from approx. 0.5 to 1 g/l, with approx. 40% of higher molecular weight proportions being found in addition. The higher molecular weight proportions include the polymeric preproinsulins.

Surprisingly, it was found within the framework of the present invention that the polymeric forms of preproinsulins adversely affect the stability of the insulins in the subsequent process stages by inducing the denaturation of the native insulins. It is known that, during the denaturation reaction chain, a first reversible step produces, from the dissolved monomeric insulin molecules, linear aggregates in which physical adhesive forces hold together the repeated units. An irreversible subsequent reaction produces, from the dissolved aggregates, stable insoluble aggregate bundles (fibrils) which in turn induce the denaturation of native insulins in an autocatalytic process. These insoluble insulin fibers are not only biologically inactive but may also cause blockage of injection needles during application of the pharmaceutical insulin preparations. In addition, they are also held responsible for immunological incompatibility reactions which can occasionally occur during therapy with insulin preparations (J. Brange et al, J. Pharm. Sc. 1997, 86, 517-525; R. E. Ratner et al., Diabetes, 39, 728-733, 1990).

In the subsequent part of the insulin preparation process, preproinsulin is converted to human insulin with the aid of the enzymes trypsin and carboxypeptidase B (see Kemmler, W., Peterson, J. D., and Steiner, D. F., J. Biol. Chem., 246 (1971) 6786-6791). Here, the linker peptide between the A and B chains (X in the formula 1) and the pre part at the amino end of the B chain ($R^1$ in the formula 1) are removed. The enzymic reaction with trypsin cleaves not only those peptide bonds whose cleavage produces human insulin but also, in a competing reaction, other peptide bonds whose cleavage produces a plurality of undesired byproducts. The formation of de-Thr insulin due to additional cleavage between amino acid residues B29 and B30 in formula 1 (see EP 0 264 250 B1) is particularly undesired. The removal of this byproduct in the subsequent purification stages results in large losses of product. In order to repress this undesired side reaction, the initial concentration of preproinsulin needs to be as high as possible, i.e. in the range from 8-25 g/l, corresponding to 1-3 mM (see EP 0 264 250 B1). This requirement contrasts with the requirement mentioned in the last but one paragraph.

From the above, it is evident that it is advantageous to introduce, between production of preproinsulin and cleavage of preproinsulin to insulin, an additional process step which removes the polymeric preproinsulins as completely as possible and, at the same time, increases the concentration of monomeric preproinsulin as much as possible. An additional condition is the need to ensure a very high yield in this process step.

It has therefore been proposed (EP 0 600 372 B1) to concentrate preproinsulin on a hydrophobic adsorber resin. The applicant was able to show in his own experiments that, although a high concentration factor of F=10-15 can be achieved, there is virtually no removal of polymeric preproinsulins. Another proposal (D. F. Steiner et al., Diabetes, 17 (1968), 725-736) mentions chromatographic purification of preproinsulin with the aid of an ion exchanger resin. In our own experiments, we were only able to achieve a concentration factor of F=5 and a removal of the higher molecular weight proportions to approx. 5%, using an anion exchanger resin. Although using a cation exchanger resin removed the higher molecular weight proportions to approx. 1%, the binding capacity of the resin for preproinsulin proved to be unsatisfactory.

Surprisingly, it was then found that the combination of a chromatography on an anion exchanger resin in flow-through mode with an immediately following chromatography on a cation exchanger resin in adsorption mode provided distinctly superior results. The present invention therefore relates to a method for effectively removing the higher molecular weight substances from an aqueous solution of preproinsulin with simultaneous high concentration of the monomeric preproinsulin.

According to the invention, a diluted aqueous solution of a preproinsulin, as is produced during the preparation process of insulin, is pumped at pH 7.0 to 9.0, preferably at pH 7.5 to 8.5, and a conductivity of from 5 to 7 mS/cm through a precolumn packed with an anion exchanger resin, for example Source 30 Q. In this case, the monomeric preproinsulin is not bound to the resin but runs through the column together with the permeate. In contrast, the majority of the higher molecular weight substances, including the polymeric preproinsulins, is adsorbed to the resin and thus removed from preproinsulin. The permeate from this precolumn, which contains the substance of interest, is adjusted in line to pH 3.0 to 5.5, preferably to pH 4.0 to 5.0, using hydrochloric acid and then pumped directly onto a second column packed with a cation exchanger resin, for example Source 30 S. Preproinsulin adsorbs to this resin and impurities are washed out of the column together with the permeate. Preproinsulin is desorbed with the aid of an elution buffer containing sodium chloride at a linearly increasing concentration of from 1 to 20 g/l, preferably 2.5 to 15.0 g/l. The purified preproinsulin is collected in a main fraction, whereas further impurities are removed in a prefraction and a postfraction. In the main fraction which contained >90% of the initial amount of preproinsulin, a concentration of from 15 to 20 g/l was measured (concentration factor F=20-25). The higher molecular weight substances were removed to a proportion of <0.1%. The preproinsulin purified in this way can be isolated from the solution intermediately by crystallization or the solution can be fed directly to the enzymic cleavage process stage.

The present invention thus relates to a method for the chromatographic purification of preproinsulin of the formula 1,

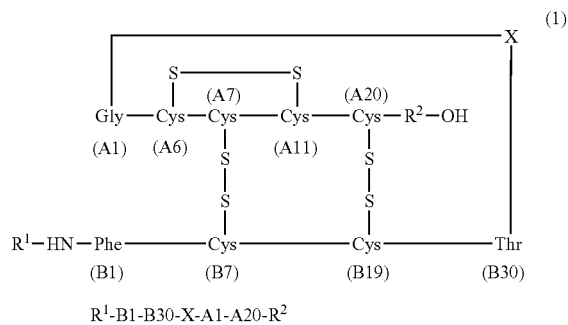

$R^1$-B1-B30-X-A1-A20-$R^2$ in which

X a) is a genetically encodable amino acid residue or
   b) is a peptide having from 2 to 35 amino acid residues, which starts and ends with in each case a basic amino acid residue, in particular Arg, and which, if it consists of more than 3 amino acid residues, starts and ends with in each case two basic amino acid residues, in particular Arg and/or Lys, $R^1$ a) is hydrogen,
   b) is a genetically encodable amino acid residue or c) is a peptide having from 2 to 15 amino acid residues,
R² is a genetically encodable amino acid residue, and and the residues A1-A20 correspond to the amino acid sequence of the A chain of human insulin or of an insulin analog and the residues B1-B30 correspond to the amino acid sequence of the B chain of human insulin or of an insulin analog;

in which method higher molecular weight substances are removed from an aqueous solution of said preproinsulin by means of a first chromatography on an anion exchanger in flow-through mode and a subsequent second chromatography on a cation exchanger in adsorption mode;

wherein said preproinsulin can have the following amino acid sequence:

```
                                            (SEQ ID NO: 2)
Ala-Thr-Thr-Ser-Thr-Gly-Asn-Ser-Ala-Arg-Phe-Val-
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys-Thr-Arg-Arg-Glu-Ala-Glu-Asp-Pro-Gln-
Val-Gly-Gln-Val-Glu-Leu-Gly-Gly-Gly-Pro-Gly-Ala-
Gly-Ser-Leu-Gln-Pro-Leu-Ala-Leu-Glu-Gly-Ser-Leu-
Gln-Lys-Arg-Gly-Ile-Val-Glu-Gln-Cys-Cys-Thr-Ser-
Ile-Cys-Ser-Leu-Tyr-Gln-Leu-Glu-Asn-Tyr-Cys-Asn;

(SEQ ID NO: 3)
Ala-Thr-Thr-Ser-Thr-Gly-Asn-Ser-Ala-Arg-Phe-Val-
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys-Thr-Arg-Arg-Glu-Ala-Glu-Asp-Pro-Gln-
Val-Gly-Gln-Val-Glu-Leu-Gly-Gly-Gly-Pro-Gly-Ala-
Gly-Ser-Leu-Gln-Pro-Leu-Ala-Leu-Glu-Gly-Ser-Leu-
Gln-Lys-Arg-Gly-Ile-Val-Glu-Gln-Cys-Cys-Thr-Ser-
Ile-Cys-Ser-Leu-Tyr-Gln-Leu-Glu-Asn-Tyr-Cys-Gly;

(SEQ ID NO: 4)
Ala-Thr-Thr-Ser-Thr-Gly-Asn-Ser-Ala-Arg-Phe-Val-
Lys-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Glu-Thr-Arg-Asp-Val-Pro-Gln-Val-Glu-Leu-
Gly-Gly-Gly-Pro-Gly-Ala-Gly-Ser-Leu-Gln-Pro-Leu-
Ala-Leu-Glu-Gly-Ser-Leu-Gln-Lys-Arg-Gly-Ile-Val-
Glu-Gln-Cys-Cys-Thr-Ser-Ile-Cys-Ser-Leu-Tyr-Gln-
Leu-Glu-Asn-Tyr-Cys-Asn.
```

The invention further relates to a method as described above for separating foreign substances from the solutions of preproinsulins which induce insulin denaturation.

The invention further relates to a method as described above, wherein the second chromatography is carried out at a pH of from 3.0 to 5.5.

The invention further relates to a method as described above, wherein the second chromatography is carried out under a pressure of from 1 to 30 bar.

The invention further relates to a method for preparing insulin by expressing nonfolded preproinsulin, comprising the steps:
a) fermentation of genetically modified microorganisms which express nonfolded preproinsulin,
b) harvesting the microorganisms and cell disruption,
c) isolating the inclusion bodies containing undissolved, nonfolded preproinsulin,
d) dissolving the preproinsulin with correct folding of the peptide chain and simultaneous closure of the disulfide bridges to give preproinsulin, and subsequently running a method for chromatographic purification of preproinsulin of the formula 1 as described above,
e) enzymic cleavage of preproinsulin to give human insulin,
f) purification of human insulin,
g) crystallization of human insulin and drying.

The contents of all references cited herein are hereby incorporated in their entirety by reference.

The above disclosure generally describes the present invention. A more complete understanding can be obtained by reference to the following specific examples which are provided herein for purposes of illustration only, and are not intended to limit the scope of the invention.

EXAMPLES

The starting solution for the purification of various preproinsulins of the formula 1, described in the following examples 1 to 3, was prepared in the known manner (EP 0 489 780 and EP 0 600 372) as follows, according to the abovementioned process stages a, b, c and d:

During fermentation of the microorganisms (process stage a), the *E. coli* cells formed inclusion bodies which contained the fusion protein having the amino acid sequence of the preproinsulin. After finishing the fermentation, the cells are isolated by centrifugation and disrupted by means of the usual high-pressure homogenization (process stage b). The insoluble inclusion bodies released in the process were isolated by centrifugation and washed with water in the centrifuge (process stage c). In the subsequent process stage d, the fusion protein inclusion bodies were dissolved in an 8 M guanidine hydrochloride solution at pH 10.8. After diluting with water and adding cysteine hydrochloride, the fusion protein was folded with closure of the 3 disulfide bridges at pH 10.8 and 4° C. to give preproinsulin of the formula 1. The solution was then adjusted to pH 5 using 10% strength hydrochloric acid, as a result of which foreign proteins were precipitated which were removed by centrifugation. The supernatant after centrifugation contained 0.6 to 0.8 g/l monomeric preproinsulin. The purity of preproinsulin, as determined by HPLC-RP analysis, was approx. 65% by area. HPLC-GPC analysis determined a proportion of approx. 45% by area higher molecular weight impurities.

HPLC-RP Analysis
Column: LiChroCART 2504 from Merck (Superspher 100-RP18e)
Instrument: Waters 2690
Software: Waters Millenium
Gradient: A: 25% by volume acetonitrile, 0.3 M NaCl in 0.05 M phosphate buffer
  pH 2.5
  B: 65% by volume acetonitrile, 0.05 M NaCl in 0.05 M phosphate buffer
  pH 2.5
  The gradient is characterized by the following amounts of buffer B according to the corresponding run times:
  0 min 4.0%; 20 min 17.0%; 30 min 37.0%; 40 min 4.0%
Temperature: 35° C.
Loading volume: 10 μl
Total run time: 55 min
Flow rate: 1.0 ml/min
Detection: 214 nm (Waters 2487)

In order to determine the preproinsulin content in the loading solution, the peak area of preproinsulin in the analyzed sample was divided by the corresponding peak area of a standard substance. In order to determine the degree of purity, the peak area of preproinsulin was divided by the sum of the peak areas of all elutable substances in the analyzed sample.

HPLC-GPC Analysis
Column: 2 columns in series, stainless steel L=300 mm; ID=7.8 mm
Instrument: pump: Waters 510/autosampler Wisp 717

Software: Waters Millenium
Stationary phase: Shodex Protein KW 802.5 120-7 diol
Separation limits: 2 000 to 80 000 dalton
Mobile phase: 30% by volume acetonitrile, 3.5 M acetic acid, pH 3.0 adjusted with aqueous ammonia
Gradient: isocratic
Temperature: room temperature
Loading volume: 100 µl
Total run time: 65 min
Flow rate: 0.5 ml/min
Detection: 276 nm (Waters 2487)

In order to determine the proportion of higher molecular substances, the peak areas of all higher molecular substances which were eluted prior to monomeric preproinsulin were divided by the sum of the peak areas of all elutable substances. The retention time for monomeric preproinsulin was determined using a standard substance.

Example 1

After completion of the abovementioned process stages a, b, c and d, a solution of preproinsulin having the following amino acid sequence was obtained from the appropriately genetically modified *E. coli* cells:

(SEQ ID NO: 2)
Ala-Thr-Thr-Ser-Thr-Gly-Asn-Ser-Ala-Arg-Phe-Val-

Asn-Gln-His-Leu-Cys-Gly-Ser-His-Leu-Val-Glu-Ala-

Leu-Tyr-Leu-Val-Cys-Gly-Glu-Arg-Gly-Phe-Phe-Tyr-

Thr-Pro-Lys-Thr-Arg-Arg-Glu-Ala-Glu-Asp-Pro-Gln-

Val-Gly-Gln-Val-Glu-Leu-Gly-Gly-Gly-Pro-Gly-Ala-

Gly-Ser-Leu-Gln-Pro-Leu-Ala-Leu-Glu-Gly-Ser-Leu-

Gln-Lys-Arg-Gly-Ile-Val-Glu-Gln-Cys-Cys-Thr-Ser-

Ile-Cys-Ser-Leu-Tyr-Gln-Leu-Glu-Asn-Tyr-Cys-Asn

Said preproinsulin corresponds to the formula 1, in which
X is a peptide chain having 35 amino acid residues with the sequence of simian C peptide,
R1 is a peptide chain having 10 amino acid residues of the sequence:

(SEQ ID NO: 5)
Ala-Thr-Thr-Ser-Thr-Gly-Asn-Ser-Ala-Arg

R2 is the amino acid residue Asn (identical to A21 of the A chain of human insulin)
A1-A20 is the peptide chain having the sequence (only A1 to A20) of the A chain of human insulin
B1-B30 is the peptide chain having the sequence of the B chain of human insulin.

The preproinsulin solution was purified using an apparatus which comprised primarily two chromatography columns arranged in series and a stirred vessel arranged in between. The stirred vessel was used to change the pH of the solution in line between the two columns.

In the first chromatography column (manufacturer: Pharmacia, diameter: 5 cm), a gel bed (bed height: 14 cm, bed volume: 275 ml) was prepared using the anion exchanger resin DEAE-Sepharose fast flow (manufacturer: Pharmacia Biotech; Prod. No. 17-0709-05). The column was operated from top to bottom and at atmospheric pressure of 1 bar. The flow rate was 2 000 ml/h. A multiway valve, a loading pump (Ismatec MV) and a bubble trap were installed upstream of the column. The following solutions were pumped onto the column successively via the multiway valve:

| | |
|---|---|
| 8.1 l | of loading solution, |
| 2.3 l | of displacement buffer, |
| 1.4 l | of washing buffer, |
| 1.4 l | of regenerating solution, |
| 2 l | of equilibration buffer. |

A UV probe (275 nm, with data recording) and another multiway valve were installed downstream of the column. Via the second multiway valve, approx. 10.2 l of permeate fraction were conducted into the abovementioned stirred vessel and, subsequently, approx. 1 l of washing fraction was conducted into a collecting vessel. The remaining permeates were discharged into the biological waste channel via the multiway valve.

The anion exchange chromatography was operated in flow-through mode, i.e. the conditions (pH 8.3; conductivity=6.1 mS/cm) were chosen such that the valuable substance preproinsulin was not bound to the gel but washed through the column together with the permeate during product application. In contrast, contaminations were adsorbed to the gel and removed with the washing buffer and the regenerating solution.

The solutions used had the following composition:

| Starting solution for column 1: | | | |
|---|---|---|---|
| Starting solution (supernatant from centrifugation) | | 8.0 l | |
| Sodium chloride solution, 25% strength (w/w) | | 100 ml | 12.5 ml/l |
| Sodium hydroxide solution, 10% (w/w) | approx. pH | 4.5 ml 8.3 | 0.6 ml/l |
| Conductivity | | 6.1 mS/cm | |
| Temperature | approx. | 5° C. | |
| Purified water | | 1 l | |
| Tris(hydroxymethyl)aminomethane | | 4.0 g/l | |
| Sodium chloride | | 2.5 g/l | |
| Hydrochloric acid, 25% strength (w/w) | approx. pH | 2.5 ml/l 8.0 | |
| Conductivity | approx. | 5.7 mS/cm | |

-continued

| | | | |
|---|---|---|---|
| Temperature | | room temperature | |
| Purified water | | 1 l | |
| Tris(hydroxymethyl)aminomethane | | 5.0 g/l | |
| Sodium chloride | | 15 g/l | |
| Hydrochloric acid, 25% strength (w/w) | approx. | 3 ml/l | |
| | pH | 8.0 | |
| Conductivity | approx. | 24 mS/cm | |
| Temperature | | room temperature | |
| Regenerating solution for columns 1 and 2: | | | |
| Purified water | | 0.91 L | |
| Sodium chloride | | 40 g | 40 g/l |
| Sodium hydroxide solution 33% strength (w/w) | | 0.09 l | 1 mol/l |
| Equilibration buffer for column 1: | | | |
| Purified water | | 1 l | |
| Tris(hydroxymethyl)aminomethane | | 5.0 g/l | |
| Sodium chloride | | 2.0 g/l | |
| Hydrochloric acid, 25% strength (w/w) | approx. | 3 ml/l | |
| | pH | 8.0 | |
| Conductivity | approx. | 5.1 mS/cm | |
| Temperature | | room temperature | |

The permeate fraction containing the valuable substance preproinsulin and the washing fraction containing the majority of the higher molecular weight impurities were collected at the column outlet:

| | | |
|---|---|---|
| 1. | approx. 10.2 l | permeate fraction (at start of loading solution, from UV value 20% (ascending) to UV value 35% (descending), during product displacement) |
| 2. | approx. 1 l | washing fraction (during loading of washing buffer, from UV value 30% (ascending slope) to UV value 40% (descending)) |

All other permeates were discharged into the biological waste channel.

The permeate fraction of the first column was adjusted to pH 3.5 with 90% strength lactic acid inline in the intermediate vessel (nominal volume: 4 l, with stirrer, pH probe and inlet tube) and then pumped directly onto the second chromatography column.

In the second chromatography column (manufacturer: Pharmacia, diameter: 5 cm), a gel bed (bed height: 10.5 cm, bed volume: 206 ml) was prepared using the cation exchanger resin Source 30 S (manufacturer: Pharmacia Biotech; Prod. No. 17-1273-04). The column was operated from top to bottom and at atmospheric pressure of 1 bar. The flow rate was likewise 2 000 ml/h. A multiway valve, a loading pump and a bubble trap were installed upstream of the column. The following solutions were pumped onto the column successively via the multiway valve:

| | |
|---|---|
| 10.2 l | loading solution (= permeate fraction of column 1, adjusted to pH 3.5) |
| 0.5 l | displacement buffer |
| 3.0 l | elution buffer A/B (equal amounts of A and B) |
| 2.3 l | regenerating solution |
| 2 l | equilibration buffer |

A UV probe (275 nm, with data recording) and another multiway valve were installed downstream of the column. Approx. 1 l of the main fraction was conducted via the second multiway valve into a collecting vessel. The remaining permeates were discharged via the multiway valve into the biological waste channel.

The cation exchanger chromatography was operated in adsorption mode, i.e. the valuable substance preproinsulin was adsorbed to the gel during product application and (after displacing the loading solution) desorbed again using the elution buffer A/B. In order to achieve an optimal purification effect, a linearly increasing sodium chloride gradient was applied in the elution buffer.

The solutions used had the following composition:

| | | | |
|---|---|---|---|
| Loading solution for column 2: | | | |
| Permeate fraction of column 1 | approx. | 10.2 l | |
| Lactic acid, 90% strength | | 14.3 ml | 1.4 ml/l |
| | pH | 3.5 | |
| Conductivity | approx. | 6.3 mS/cm | |
| Temperature | approx. | 5° C. | |
| Displacement buffer for column 2: | | | |
| Purified water | | 1 l | |
| Lactic acid, 90% strength | | 8.3 ml | 0.1 mol/l |
| Sodium chloride | | 2.5 g | 2.5 g/l |
| Sodium hydroxide solution, 10% strength (w/w) | approx. | 8 ml | |
| | pH | 3.5 | |

-continued

| | | | |
|---|---|---|---|
| Conductivity | approx. | 8 mS/cm | |
| Temperature | | room temperature | |

Elution buffer A for column 2:

The elution buffer A is identical to the displacement buffer for column 2.
Elution buffer B for column 2:

| | | | |
|---|---|---|---|
| Purified water | | 1 l | |
| Lactic acid, 90% strength | | 8.3 ml | 0.1 mol/l |
| Sodium chloride | | 15.0 g | 15.0 g/l |
| Sodium hydroxide solution, 10% strength (w/w) | approx. pH | 7 ml 3.5 | |
| Conductivity | approx. | 25 mS/cm | |
| Temperature | | room temperature | |

Regeneration solution for columns 1 and 2:

| | | | |
|---|---|---|---|
| Purified water | | 0.91 l | |
| Sodium chloride | | 40 g | 40 g/l |
| Sodium hydroxide solution, 33% strength (w/w) | | 0.09 l | 1 mol/l |

Equilibrium buffer for column 2:

| | | | |
|---|---|---|---|
| Purified water | | 1 l | |
| Lactic acid, 90% strength | | 8.3 g | 0.1 mol/l |
| Sodium chloride | | 2.9 g/l | |
| Sodium hydroxide solution 10% strength (w/w) | approx. pH | 9 ml 3.5 | |
| Conductivity | approx. | 8.5 mS/cm | |
| Temperature | | room temperature | |

The main fraction which contained the valuable substance preproinsulin was collected at the column outlet:

| | |
|---|---|
| approx. 1.0 l | main fraction (during elution, from UV value 65% (ascending) to UV value 76% (descending)) |

All other permeates were discharged into the biological waste channel.

FIG. 2 depicts the UV diagram measured at the outlet of column 2.

In the purified solution (main fraction column 2), 15 g/l preproinsulin with a degree of purity of 89% by area were measured (HPLC-RP analysis). The yield was 91%, based on the amount of preproinsulin in the starting solution. Higher molecular proportions of 0.2% by area were determined by HPLC-GPC analysis.

Example 2

After completion of the abovementioned process stages a, b, c and d, a solution of preproinsulin having the following amino acid sequence is obtained from the appropriately genetically modified *E. coli* cells:

```
                                          (SEQ ID NO: 3)
Ala-Thr-Thr-Ser-Thr-Gly-Asn-Ser-Ala-Arg-Phe-Val-

Asn-Gln-His-Leu-Cys-Gly-Ser-His-Leu-Val-Glu-Ala-

Leu-Tyr-Leu-Val-Cys-Gly-Glu-Arg-Gly-Phe-Phe-Tyr-

Thr-Pro-Lys-Thr-Arg-Arg-Glu-Ala-Glu-Asp-Pro-Gln-

Val-Gly-Gln-Val-Glu-Leu-Gly-Gly-Gly-Pro-Gly-Ala-

Gly-Ser-Leu-Gln-Pro-Leu-Ala-Leu-Glu-Gly-Ser-Leu-
```

-continued
```
Gln-Lys-Arg-Gly-Ile-Val-Glu-Gln-Cys-Cys-Thr-Ser-

Ile-Cys-Ser-Leu-Tyr-Gln-Leu-Glu-Asn-Tyr-Cys-Gly
```

Said preproinsulin corresponds to the formula 1, in which
X is a peptide chain having 35 amino acid residues with the sequence of simian C peptide,
R1 is a peptide chain having 10 amino acid residues of the sequence:

```
                                          (SEQ ID NO: 5)
Ala-Thr-Thr-Ser-Thr-Gly-Asn-Ser-Ala-Arg
```

R2 is the amino acid residue Gly
A1-A20 is the peptide chain having the sequence (only A1 to A20) of the A chain of human insulin
B1-B30 is the peptide chain having the sequence of the B chain of human insulin.

The preproinsulin solution was purified by again using an apparatus which comprised primarily two chromatography columns arranged in series and a stirred vessel arranged in between. The stirred vessel was used to change the pH of the solution inline between the two columns. The apparatuses for the second chromatography stage were designed for pressure stability.

The chromatography on column 1 and the pH-switching in the intermediate vessel were carried out as described in example 1 so that the description and the values will not be repeated here.

In the second chromatography column (manufacturer: Prochrom, diameter 5 cm, material: stainless steel), a gel bed (bed height: 10 cm, bed volume: 196 ml) was prepared using the cationic exchanger Source 30 S (manufacturer Pharmacia Biotech; prod. No.: 17-1273-04). The column was operated from top to bottom and at a working pressure of 10 bar. The flow rate was 3 500 ml/h. A multiway valve, a loading pump (manufacturer: Besta; type: HD2-300) were installed upstream of the column. The following solutions were pumped onto the column successively via the multiway valve:

| | |
|---|---|
| 10.2 l | loading solution (= permeate fraction of column 1, adjusted to pH 4.6) |
| 0.5 l | displacement buffer |
| 3.0 l | elution buffer A/B (equal amounts of A and B) |
| 2.3 l | regenerating solution |
| 2 l | equilibration buffer |

A UV probe (275 nm, with data recording) and another multiway valve were installed downstream of the column. The main fraction containing the purified preproinsulin was conducted via the second multiway valve into a collecting vessel. The remaining permeates were discharged via the multiway valve into the biological waste channel.

The cation exchanger chromatography was operated in adsorption mode, i.e. the valuable substance preproinsulin was adsorbed to the gel during product application and (after displacing the loading solution) desorbed again using the elution buffer A/B. In order to achieve an optimal purification effect, a linearly increasing sodium chloride gradient was applied in the elution buffer.

The solutions used had the following composition:

| Loading solution for column 2: | | | |
|---|---|---|---|
| Permeate fraction of column 1 | approx. | 10.2 l | |
| Lactic acid, 90% strength | | 12.2 ml | 1.2 ml/l |
| | pH | 4.6 | |
| Conductivity | approx. | 6.7 mS/cm | |
| Temperature | approx. | 5° C. | |

| Displacement buffer for column 2: | | | |
|---|---|---|---|
| Purified water | | 1 l | |
| Lactic acid, 90% strength | | 8.3 ml | 0.1 mol/l |
| Sodium chloride | | 2.5 g | 2.5 g/l |
| Sodium hydroxide solution, 10% strength (w/w) | approx. pH | 27 ml 4.6 | |
| Conductivity | approx. | 8 mS/cm | |
| Temperature | | room temperature | |

Elution buffer A for column 2:

The elution buffer A is identical to the displacement buffer for column 2.

| Elution buffer B for column 2: | | | |
|---|---|---|---|
| Purified water | | 1 l | |
| Lactic acid, 90% strength | | 8.3 ml | 0.1 mol/l |
| Sodium chloride | | 15.0 g | 15.0 g/l |
| Sodium hydroxide solution, 10% strength (w/w) | approx. pH | 27 ml 4.6 | |
| Conductivity | approx. | 25 mS/cm | |
| Temperature | | room temperature | |

| Regeneration solution for columns 1 and 2: | | | |
|---|---|---|---|
| Purified water | | 0.91 l | |
| Sodium chloride | | 40 g | 40 g/l |
| Sodium hydroxide solution, 33% strength (w/w) | | 0.09 l | 1 mol/l |

| Equilibrium buffer for column 2: | | | |
|---|---|---|---|
| Purified water | | 1 l | |
| Lactic acid, 90% strength | | 8.3 g | 0.1 mol/l |
| Sodium chloride | | 2.9 g/l | |
| Sodium hydroxide solution 10% strength (w/w) | approx. pH | 26 ml 4.6 | |
| Conductivity | approx. | 8.7 mS/cm | |
| Temperature | | room temperature | |

The main fraction which contained the valuable substance preproinsulin was collected at the column outlet:

| | |
|---|---|
| approx. 0.9 l | main fraction (during elution, from UV value 65% (ascending) to UV value 76% (descending)) |

All other permeates were discharged into the biological waste channel. In the purified solution (main fraction from column 2), 17 g/l preproinsulin with a degree of purity of 93% by area were measured (HPLC-RP analysis). The yield was 92%, based on the amount of preproinsulin in the starting solution. Higher molecular weight proportions of <0.1% by area were determined by HPLC-GPC analysis.

Example 3

After completion of the abovementioned process stages a, b, c and d, a solution of preproinsulin having the following amino acid sequence is obtained from the appropriately genetically modified *E. coli* cells:

(SEQ ID NO: 4)
Ala-Thr-Thr-Ser-Thr-Gly-Asn-Ser-Ala-Arg-Phe-Val-

Lys-Gln-His-Leu-Cys-Gly-Ser-His-Leu-Val-Glu-Ala-

Leu-Tyr-Leu-Val-Cys-Gly-Glu-Arg-Gly-Phe-Phe-Tyr-

Thr-Pro-Glu-Thr-Arg-Asp-Val-Pro-Gln-Val-Glu-Leu-

Gly-Gly-Gly-Pro-Gly-Ala-Gly-Ser-Leu-Gln-Pro-Leu-

Ala-Leu-Glu-Gly-Ser-Leu-Gln-Lys-Arg-Gly-Ile-Val-

Glu-Gln-Cys-Cys-Thr-Ser-Ile-Cys-Ser-Leu-Tyr-Gln-

Leu-Glu-Asn-Tyr-Cys-Asn

Said preproinsulin corresponds to the formula 1, where X is a peptide chain having 29 amino acid residues with the sequence:

(SEQ ID NO: 1)
Arg-Asp-Val-Pro-Gln-Val-Glu-Leu-Gly-Gly-Gly-Pro-

Gly-Ala-Gly-Ser-Leu-Gln-Pro-Leu-Ala-Leu-Glu-Gly-

Ser-Leu-Gln-Lys-Arg

R1 is a peptide chain having 10 amino acid residues with the sequence:

(SEQ ID NO: 5)
Ala-Thr-Thr-Ser-Thr-Gly-Asn-Ser-Ala-Arg,

R2 is the amino acid residue Asn (A21 of the A chain of human insulin),
A1-A20 is a peptide chain with the sequence (only A1 to A20) of the A chain of human insulin,
B1-B30 [lacuna] peptide chain with a sequence similar to the B chain of human insulin, i.e. with Lys replacing Val in position B3 and Glu replacing Lys in position B29.

The preproinsulin solution was purified using the same apparatus used in example 1.

This time, the anion exchanger resin Source 30 Q (manufacturer: Pharmacia Biotech; Prod.-No.: 17-1275-04) was used for the chromatography on column 1. Regeneration of this gel required twice the amount of regenerating solution compared to examples 1 and 2. The remaining parameters of the first chromatography, such as composition and volumes of the solutions, were the same as those described in examples 1 and 2.

Likewise, the pH-switching in the intermediate vessel was carried out as described in example 1.

The second chromatography was this time carried out with a working pressure of 15 bar. All other parameters of the second chromatography were identical to those described in example 2.

In the purified solution (main fraction from column 2), 17 g/l preproinsulin with a degree of purity of 92.5% by area were measured (HPLC-RP analysis). The yield was 91%, based on the amount of preproinsulin in the starting solution. Higher molecular weight proportions of <0.1% by area were determined by HPLC-GPC analysis.

Denaturation Assay

The denaturation assay (table 1) shows that the higher molecular weight, polymeric forms of preproinsulins, as produced during the folding reaction, can induce denaturation of native insulin.

In the denaturation assay, native insulin glargine, an Aventis Deutschland GmbH product, which is obtained after enzymic cleavage of the preproinsulin described in example 2, was crystallized. Surprisingly, we were able to show in all experiments that, under the conditions of insulin glargine crystallization (pH 6.1 and 26° C.), denaturation of native insulin occurs when substances which can induce insulin denaturation are added to the crystallization mixture.

A standard solution of the following composition was prepared for the crystallization mixtures:

| | |
|---|---|
| Insulin glargine | 5 g/l |
| Citric acid | 5.2 mmol/l |
| Zinc chloride | 3 mmol/l |
| Sodium chloride | 0.5 g/l |
| n-Propanol | 7% (v/v) |
| Purified water to | 500 ml |
| using 1 N hydrochloric acid, pH | 3 |

The solution was filtered through a membrane filter with a pore width of 0.1 µm.

In the denaturation assay, this acidic standard solution was admixed with solutions of the various assay substances: the washing fraction of column 1 which contained the removed polymeric forms of preproinsulins at a concentration of 5 g/l or the main fraction of column 2 which contained purified preproinsulin at a concentration of 15 and, respectively, 17 gA. For further proof that the phenomena observed were caused by insulin denaturation, 10 ml of a 0.1% strength aqueous stock solution of Poloxamer 171 were added. Poloxamer 171 is known to be able to suppress insulin denaturation at hydrophobic interfaces (H. Thurow and K. Geisen, Diabetologia (1984) 27, 212-218 and EP 0 018 609).

The solutions were then heated to 26° C. and adjusted to pH 6.1 with 10% strength sodium hydroxide solution with stirring, resulting in the precipitation of amorphous insulin. The amorphous suspension was stirred at 26° C. for 50 hours. After this time, all mixtures contained insulin crystals.

The mixtures were analyzed by evaluating samples under the microscope, looking for the appearance of amorphous particles (veils) in the background or between the insulin crystals. In addition, each mixture was divided into two parts of approximately the same size. The first part was introduced into a 250 ml measuring cylinder in order to investigate the sedimentation behavior, and after leaving the mixtures at room temperature for 60 min, sediment volume and supernatant clarity were evaluated. The second part was adjusted to pH 3 with 1 N hydrochloric acid, and, after the insulin crystals had dissolved, the clarity of the resulting solution was evaluated.

Table 1 shows the result of the denaturation assay. In the control samples 174 A and 188 A without addition of the polymer fraction, no denaturation had been observed. Under the microscope, crystals were visible against a clear background. After 60 minutes, the crystals had sedimented, resulting in a compact sediment and a clear supernatant. After dissolving the crystals at pH 3, a clear solution had been produced. In contrast, the samples 174 B, 188 B and 174 C, in the case of which 1 ml and, respectively, 5 ml of polymer fraction had been added to the crystallization mixture, showed a distinct denaturation of insulin glargine. Under the microscope, an amorphous veil was visible between the crystals. In the sedimentation assay, voluminous sediments having a sediment volume of from 50 to 90 ml (from 250 ml of crystal suspension) had been produced. After redissolving the crystals at pH 3, more or less opaque amorphous suspensions had been produced. In the presence of 20 ppm of Poloxamer 171, no denaturation had been observed with the addition of 1 ml of polymer solution (188 C). In the assay mixtures 174 D, 174 E and 174 F which had been admixed with purified preproinsulins (main fraction of column 2 from examples 1, 2 and 3), likewise no denaturation of insulin glargine was observed.

Similar results, not shown here, were obtained in an analogous denaturation assay in which human insulin was crystallized.

TABLE 1

Influence of higher molecular weight impurities on insulin glargine denaturation

| Crystallization mixture No. | Additions to the crystallization mixture | Microscopic image background appearance (between rhombohedral crystals) | Appearance after dissolving the crystals at pH 3 | Sedimentation behavior of crystal suspension |
|---|---|---|---|---|
| 174 A | none | clear | clear | + + + |
| 174 B | 1 ml of washing fraction, column 1* | amorphous particles | slightly opaque | + - - |
| 174 C | 5 ml of washing fraction, column 1* | more amorphous particles | opaque | - - - |
| 174 D | 1 ml of main fraction, example 1** | clear | clear | + + + |
| 174 E | 1 ml of main fraction, example 2*** | clear | clear | + + + |
| 174 F | 1 ml of main fraction, example 3**** | clear | clear | + + + |
| 188 A | none | clear | clear | + + + |
| 188 B | 1 ml of washing fraction, column 1* | amorphous particles | opaque | - - - |
| 188 C | 1 ml of washing fraction, column 1* and 20 ppm Poloxamer 171 | occasional amorphous particles | clear | + + + |

Crystallization mixtures of in each case 500 ml with 2 500 mg of insulin glargine (= 5 g/l).
*The washing fraction of column 1 from example 2 contains 5 g/l protein.
**The main fraction of column 2 from example 1 contains 15 g/l preproinsulin
***The main fraction of column 2 from example 2 contains 17 g/l preproinsulin
****The main fraction of column 2 from example 3 contained 17 g/
+ + + = After approx. 60 min, 3 to 5 ml of sediment from 250 ml of suspension.
- - - = After approx. 60 min, up to 90 ml of sediment from 250 ml of suspension.

SEQUENCE LISTING

<160> NUMBER OF SEQ ID NOS: 4

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence:C-Peptid

<400> SEQUENCE: 1

Arg Asp Val Pro Gln Val Glu Leu Gly Gly Gly Pro Gly Ala Gly Ser
 1               5                  10                  15

Leu Gln Pro Leu Ala Leu Glu Gly Ser Leu Gln Lys Arg
            20                  25

<210> SEQ ID NO 2
<211> LENGTH: 96
<212> TYPE: PRT
<213> ORGANISM: Artificial Sequence
<220> FEATURE:
<223> OTHER INFORMATION: Description of Artificial Sequence:
      Preproinsulin I

<400> SEQUENCE: 2

Ala Thr Thr Ser Thr Gly Asn Ser Ala Arg Phe Val Asn Gln His Leu
 1               5                  10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Pro Gln
        35                  40                  45

Val Gly Gln Val Glu Leu Gly Gly Gly Pro Gly Ala Gly Ser Leu Gln
    50                  55                  60

```
Pro Leu Ala Leu Glu Gly Ser Leu Gln Lys Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence:
      Preproinsulin II

<400> SEQUENCE: 3

Ala Thr Thr Ser Thr Gly Asn Ser Ala Arg Phe Val Asn Gln His Leu
  1               5                  10                  15

Cys Gly Ser His Leu Val Glu Ala Leu Tyr Leu Val Cys Gly Glu Arg
                20                  25                  30

Gly Phe Phe Tyr Thr Pro Lys Thr Arg Arg Glu Ala Glu Asp Pro Gln
            35                  40                  45

Val Gly Gln Val Glu Leu Gly Gly Gly Pro Gly Ala Gly Ser Leu Gln
        50                  55                  60

Pro Leu Ala Leu Glu Gly Ser Leu Gln Lys Arg Gly Ile Val Glu Gln
65                  70                  75                  80

Cys Cys Thr Ser Ile Cys Ser Leu Tyr Gln Leu Glu Asn Tyr Cys Gly
                85                  90                  95

<210> SEQ ID NO 4
<211> LENGTH: 90
<212> TYPE: PRT
<213> ORGANISM: Artificial Sequence
<220> FEATURE:
<223> OTHER INFORMATION: Description of Artificial Sequence:
      Preproinsulin III

<400> SEQUENCE: 4

Ala Thr Thr Ser Thr Gly Asn Ser Ala Arg Phe Val Lys Gln His Leu
  1               5                  10                  15

Cys Gly Ser His Leu Val Glu Ala Leu Tyr Leu Val Cys Gly Glu Arg
                20                  25                  30

Gly Phe Phe Tyr Thr Pro Glu Thr Arg Asp Val Pro Gln Val Glu Leu
            35                  40                  45

Gly Gly Gly Pro Gly Ala Gly Ser Leu Gln Pro Leu Ala Leu Glu Gly
        50                  55                  60

Ser Leu Gln Lys Arg Gly Ile Val Glu Gln Cys Cys Thr Ser Ile Cys
65                  70                  75                  80

Ser Leu Tyr Gln Leu Glu Asn Tyr Cys Asn
                85                  90
```

We claim:

1. A method for the chromatographic purification of preproinsulin of the formula 1,

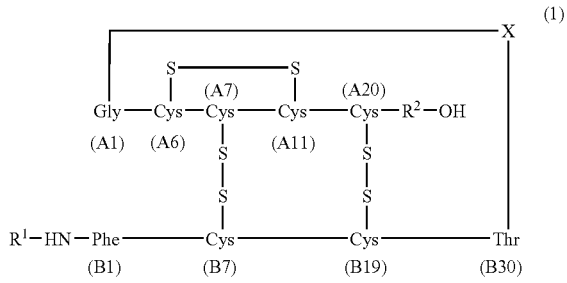

wherein
X a) is a genetically encodable amino acid residue or
  b) is a peptide having from 2 to 35 amino acid residues, which starts and ends with in each case a basic amino acid residue, in particular Arg, and which, if it consists of more than 3 amino acid residues, starts and ends with in each case two basic amino acid residues, in particular Arg and/or Lys,
$R^1$ a) is hydrogen,
  b) is a genetically encodable amino acid residue or
  c) is a peptide having from 2 to 15 amino acid residues,
$R^2$ is a genetically encodable amino acid residue, and
  the residues A1-A20 correspond to the amino acid sequence of the A chain of human insulin or of an insulin analog and the residues B1-B30 correspond to the amino acid sequence of the B chain of human insulin or of an insulin analog;

wherein said method for chromatographic purification of preproinsulin comprises:

removing higher molecular weight substances from an aqueous solution of said preproinsulin by means of a first chromatography on an anion exchanger in flow-through mode and a subsequent second chromatography on a cation exchanger in adsorption mode and wherein said preproinsulin of formula (1) is consisting of the following amino acid sequence:

```
                                      (SEQ ID NO: 3)
Ala-Thr-Thr-Ser-Thr-Gly-Asn-Ser-Ala-Arg-Phe-Val-

Asn-Gln-His-Leu-Cys-Gly-Ser-His-Leu-Val-Glu-Ala-

Leu-Tyr-Leu-Val-Cys-Gly-Glu-Arg-Gly-Phe-Phe-Tyr-

Thr-Pro-Lys-Thr-Arg-Arg-Glu-Ala-Glu-Asp-Pro-Gln-

Val-Gly-Gln-Val-Glu-Leu-Gly-Gly-Gly-Pro-Gly-Ala-

Gly-Ser-Leu-Gln-Pro-Leu-Ala-Leu-Glu-Gly-Ser-Leu-
```

```
                  -continued
Gln-Lys-Arg-Gly-Ile-Val-Glu-Gln-Cys-Cys-Thr-Ser- Ile-Cys-Ser-Leu-Tyr-Gln-Leu-Glu-Asn-Tyr-Cys-Gly
``` and wherein

X is a peptide chain having 35 amino acid residues with the sequence of simian C peptide, R1 is a peptide chain having 10 amino acid residues with the sequence Ala-Thr-Thr-Ser-Thr-Gly-Asn-Ser-Ala-Arg (SEQ ID NO: 5), R2 is the amino acid residue Gly, A1-A20 is a peptide chain with the sequence (only A1 to A20) of the A chain of human insulin, B1-B30 is a peptide chain having the sequence of the B chain of human insulin.

2. The method of claim 1, which comprises separating foreign substances from said aqueous solution of preproinsulin which induce insulin denaturation.

3. The method of claim 1 wherein said second chromatography is carried out at a pH of from 3.0 to 5.5.

4. The method of claim 1 wherein said second chromatography is carried out under a pressure of from 1 to 30 bar.

* * * * *

UNITED STATES PATENT AND TRADEMARK OFFICE
CERTIFICATE OF CORRECTION

| | | |
|---|---|---|
| PATENT NO. | : 7,803,763 B2 | Page 1 of 3 |
| APPLICATION NO. | : 11/305508 | |
| DATED | : September 28, 2010 | |
| INVENTOR(S) | : Horst Thurow et al. | |

It is certified that error appears in the above-identified patent and that said Letters Patent is hereby corrected as shown below:

On the title page, in field (54), in column 1, in "Title", line 1, delete "OF" and insert -- FOR --, therefor.

In column 1, line 1, delete "OF" and insert -- FOR --, therefor.

In column 1, line 3, below Title insert -- CROSS REFERENCE TO RELATED APPLICATIONS This application is a continuation of U.S. application Ser. No. 10/632,414 filed on Aug. 1, 2003, now abandoned and claims benefit from U.S. Provisional Application No. 60/433,726, filed on Dec. 16, 2002, each of which is incorporated herein by reference. --.

In column 2, line 30, before "the" delete "and".

In column 6, line 39, delete "2504" and insert -- 250-4 --, therefor.

In column 6, line 67, delete "autosampler" and insert -- autosampler: --, therefor.

In column 11, line 40-41, below "channel." delete "FIG. 2 depicts the UV diagram measured at the outlet of column 2.".

In column 12, line 62, delete "diameter" and insert -- diameter: --, therefor.

In column 12, line 64, delete "(manufacturer" and insert -- (manufacturer: --, therefor.

In column 16, line 30, delete "gA." and insert -- g/l. --, therefor.

Signed and Sealed this
Tenth Day of July, 2012

David J. Kappos
*Director of the United States Patent and Trademark Office*

CERTIFICATE OF CORRECTION (continued)
U.S. Pat. No. 7,803,763 B2

In the Claims:

Delete "1. A method for the chromatographic purification of preproinsulin of the formula 1,

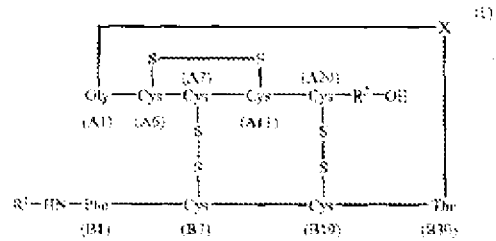

wherein
    X a) is a genetically encodable amino acid residue or
    b) is a peptide having from 2 to 35 amino acid residues,
    which starts and ends with in each case a basic amino
    acid residue, in particular Arg, and which, if it consists
    of more than 3 amino acid residues, starts and ends
    with in each case two basic amino acid residues, in
    particular Arg and/or Lys,
$R^1$ a) is hydrogen,
    b) is a genetically encodable amino acid residue or
    c) is a peptide having from 2 to 15 amino acid residues,
$R^2$ is a genetically encodable amino acid residue, and
    the residues A1-A20 correspond to the amino acid
    sequence of the A chain of human insulin or of an insulin
    analog and the residues B1-B30 correspond to
    the amino acid sequence of the B chain of human
insulin or of an insulin analog;
wherein said method for chromatographic purification
    of preproinsulin comprises:
removing higher molecular weight substances from an
    aqueous solution of said preproinsulin by means of a
    first chromatography on an anion exchanger in flowthrough
    mode and a subsequent second chromatography
    on a cation exchanger in adsorption mode and
wherein said preproinsulin of formula (I) is consisting of
    the following amino acid sequence:
                            (SEQ ID NO, 3)
Ala-Thr-Thr-Ser-Thr-Gly-Asn-Ser-Ala-Arg-Phe-Val-
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys-Thr-Arg-Arg-Glu-Ala-Glu-Asp-Pro-Gln-
Val-Gly-Gln-Val-Glu-Leu-Gly-Gly-Gly-Pro-Gly-Ala-
Gly-Ser-Leu-Gln-Pro-Leu-Ala-Leu-Glu-Gly-Ser-Leu-
Gln-Lys-Arg-Gly-Ile-Val-Glu-Gln-Cys-Cys-Thr-Ser-
Ile-Cys-Ser-Leu-Tyr-Gln-Leu-Glu-Asn-Tyr-Cys-Gly
and wherein
    X is a peptide chain having 35 amino acid residues with the

CERTIFICATE OF CORRECTION (continued)

sequence of simian C peptide,
R1 is a peptide chain having 10 amino acid residues with
the sequence Ala-Thr-Thr-Ser- Thr-Gly-Asn-Ser-AlaArg
(SEQ ID NO: 5),
R2 is the amino acid residue Gly,
A1-A20 is a peptide chain with the sequence (only A1 to
A20) of the A chain of human insulin,
B1-B30 is a peptide chain having the sequence of the B
chain of human insulin." and insert -- 1. A method for the chromatographic purification of the preproinsulin of SEQ ID NO:3,
wherein said method comprises:
removing higher molecular weight substances from an aqueous solution of said preproinsulin
by means of a first chromatography on an anion exchanger in flowthrough
mode and a subsequent second chromatography on a cation exchanger
in adsorption mode and
wherein SEQ ID NO: 3 is:

Ala-Thr-Thr-Ser-Thr-Gly-Asn-Ser-Ala-Arg-Phe-Val-
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys-Thr-Arg-Arg-Glu-Ala-Glu-Asp-Pro-Gln-
Val-Gly-Gln-Val-Glu-Leu-Gly-Gly-Gly-Pro-Gly-Ala-
Gly-Ser-Leu-Gln-Pro-Leu-Ala-Leu-Glu-Gly-Ser-Leu-
Gln-Lys-Arg-Gly-Ile-Val-Glu-Gln-Cys-Cys-Thr-Ser-
Ile-Cys-Ser-Leu-Tyr-Gln-Leu-Glu-Asn-Tyr-Cys-Gly.                    --, therefor.